(12) United States Patent
Andrey

(10) Patent No.: US 8,129,570 B2
(45) Date of Patent: Mar. 6, 2012

(54) PROCESS FOR THE PREPARATION OF 1,4-DIALKYL-2,3-DIOL-1,4-BUTANEDIONE

(75) Inventor: Olivier Andrey, Founex (CH)

(73) Assignee: Firmenich SA, Geneva (CH)

( * ) Notice: Subject to any disclaimer, the term of this patent is extended or adjusted under 35 U.S.C. 154(b) by 351 days.

(21) Appl. No.: 12/598,800

(22) PCT Filed: Apr. 30, 2008

(86) PCT No.: PCT/IB2008/051678
§ 371 (c)(1),
(2), (4) Date: Nov. 4, 2009

(87) PCT Pub. No.: WO2008/142592
PCT Pub. Date: Nov. 27, 2008

(65) Prior Publication Data
US 2010/0137620 A1 Jun. 3, 2010

(30) Foreign Application Priority Data
May 24, 2007 (EP) .................................. 07108802

(51) Int. Cl.
C07C 45/45 (2006.01)
C07C 49/12 (2006.01)
C07C 49/17 (2006.01)
C07D 307/60 (2006.01)
(52) U.S. Cl. ................. 568/413; 568/390; 549/471
(58) Field of Classification Search .............. 568/390, 568/413; 549/477
See application file for complete search history.

(56) References Cited

U.S. PATENT DOCUMENTS
5,009,753 A 4/1991 Hermeling et al. ............. 204/75
2007/0167656 A1 7/2007 Naef et al. .................... 568/392

FOREIGN PATENT DOCUMENTS
CH 474 501 6/1969
WO WO 2006/048795 A1 5/2006

OTHER PUBLICATIONS

International Search Report, application No. PCT/IB2008/051678, mailed Nov. 5, 2008.
Bassignani et al., "Novel Applications of the Potassium Chlorate-Osmium Tetroxide Oxidizing System. Synthesis of α-Dicarbonyl Derivatives from Acetylenic Compounds. Synthesis of 2,3-Dihydroxy-1,4-dione from a 2,5-Dialkylfuran," J. Org. Chem., vol. 43, No. 21, pp. 4245-4247 (1978).
Briggs et al., "Synthesis of 4-Hydroxy-2,5-dimethylfuran-3(2H)-one (Furaneol) from (2R,3R)-Tartaric Acid," J. Chem. Soc., Perkin Trans. 1, pp. 795-798 (1985).
Büchi et al., "Syntheses of 2,5-Dimethyl-4-hydroxy-2,3-dihydrofuran-3-one (Furaneol), a Flavor Principle of Pineapple and Strawberry," J. Org. Chem., vol. 88, No. 1, pp. 123-125 (1973).
Micheel, "Übergang von der Hexosereihe in die Cyclitreihe," Aus dem Allgem. Chemischen Universitäts-Laboratorium Göttingen, pp. 77-98 (1932).

*Primary Examiner* — Bernard Dentz
(74) *Attorney, Agent, or Firm* — Winston & Strawn LLP

(57) ABSTRACT

The present invention relates to a process for the preparation of compounds of a 1,4-dialkyl-2,3-diol-1,4-butanedione by a acidic aldol condensation between an alkyl glyoxal and an α-hydroxy ketone.

9 Claims, No Drawings

PROCESS FOR THE PREPARATION OF 1,4-DIALKYL-2,3-DIOL-1,4-BUTANEDIONE

This application is a 371 filing of International Patent Application PCT/IB2008/051678 filed Apr. 30, 2008.

TECHNICAL FIELD

The present invention relates to the field of organic synthesis and more particularly to a process for the preparation of compounds of formula (I) by the aldol condensation between an alkyl glyoxal (II) and an acetol derivative (III), said condensation being promoted by specific acidic conditions, according to Scheme (1):

Scheme 1: Aldol Condensation of Glyoxals and Acetols According to the Invention

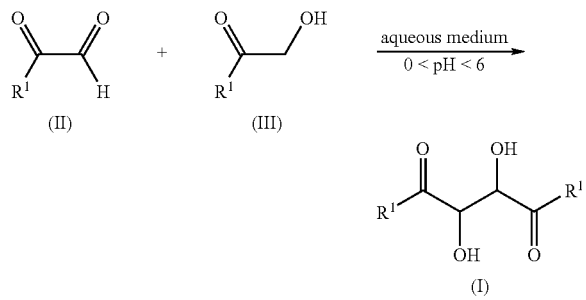

wherein $R^1$ represents a linear or branched $C_1$ to $C_5$ alkyl group.

PRIOR ART

The compounds of formula (I), as defined below, can be useful as starting material for the construction of compounds having a more complex skeleton, such as 4-hydroxy-2,5-dimethyl-3(2H)-furanone (known as Furaneol®, Trademark of Firmenich SA).

Various processes for the preparation of compounds of formula (I) have been reported, for example Briggs et al, J. Chem. Soc. Perkin. Trans. I, 1985, 795 relates to a multistep synthesis of the 3,4-dihydroxyhexane-2,5-dione starting from tartaric acid, or Bassignani et al, J. Org. Chem., 1978, 43, 4245 relates to the synthesis of the 3,4-dihydroxyhexane-2,5-dione by oxidizing the expensive 2,5-dimethylfuran with the toxic and expensive $KClO_3/OsO_4$ system. Another reported method to synthesize compounds (I) is the reductive dimerisation of glyoxals promoted by various methods (for instance see Büchi et al, J. Org. Chem., 1973, 38, 123).

More recently, F. Naef and al. (WO 2006/048795) reported a method of preparation by aldol condensation between an alkyl glyoxal and an acetol derivative, this method requiring the mandatory presence of specific catalysts, such as $Zn(AcO)_2$. The reported method suffers from relatively low yields and the mandatory use of metal salts as catalysts, as well as from very long reaction times.

The above-mentioned methods of preparation are in general quite long and expensive or require the use of a heavy metal which implies problems of purification of the final product and of waste treatment. Furthermore, frequently the yields are low.

Therefore, there is still a need for a method of preparation that is more environmental friendly, more direct or fast and providing good yields.

DESCRIPTION OF THE INVENTION

In order to overcome the problems aforementioned, and provide also an alternative process for the preparation of compounds of formula (I), the present invention relates to a process aimed at the synthesis of compounds (I) in a single step and with good yields.

The process of the invention concerns more specifically the aldol condensation between an alkyl glyoxal (II) and an acetol derivative (III) under acidic condition without requiring the mandatory presence of a metal salt, contrary to the prior art aldol process.

Therefore, the process of the invention concerns the preparation of a compound of formula

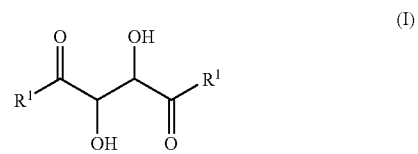

wherein each $R^1$ represents, simultaneously or independently from each other, a linear or branched $C_1$ to $C_5$ alkyl group, by the aldol condensation, in an aqueous reaction medium, between a glyoxal of formula

wherein $R^1$ has the same meaning as defined above, and an α-hydroxy ketone of formula

wherein $R^1$ has the same meaning as defined above, said process being characterized in that said aqueous reaction medium has a pH comprised between 0 and 6, and that the process is carried out at a temperature comprised between 50° C. and the reflux temperature.

The invention's process does not require metal catalysts, and therefore can be carried out in the absence of such compounds. In particular the catalysts of formula $FeX_3$ or $MX_2$, wherein M is $Zn^{2+}$, $Mg^{2+}$, $Cu^{2+}$, $Fe^{2+}$ or $Ca^{2+}$ and X is a $C_1$-$C_7$ carboxylate, a halide or an acetylacetonate derivative of formula $[R^2COCHCOR^2]^-$, $R^2$ representing a $C_1$-$C_3$ alkyl group or a phenyl group, as described in WO 2006/048795 are not required. According to particular embodiment of the invention, said process can be also free of any useful amount of catalysts of formula $M(X)n$, wherein n is 2 or 3, X is as defined above and M is a transition or alkaline-earth metal.

As mentioned above the process takes place within a specific pH range of the aqueous reaction medium, i.e. form a weakly acidic to strong acidic medium.

According to an embodiment of the invention the present process is preferably carried out in a reaction medium having a pH comprised between 0 and 4.6, preferably between 0.0 and 3.0, or even comprised between 0.5 and 2.3.

The pH can be set up to the desired value by adding into the reaction medium an acid or a base, in such a case the pH of the medium once fixed may change within the desired range during the reaction. Mixtures of acids can also be used. Alternatively, the pH of the medium can be regulated and maintained throughout the reaction by using a buffer.

It is useful also to note here that an aqueous reaction medium consisting of water and compounds (II) and (III), is as such already acidic and therefore in some case it may not be necessary to add an acid to acidify the aqueous reaction medium, but rather it may be necessary to add a base to increase the pH to the desired value.

Any type of acid can be used, i.e. organic, inorganic or acidic resin. Such acids are well known by a parson skilled in the art. As typical examples, one may cite the following: HCl, $H_2SO_4$, $H_3PO_4$, $C_1$-$C_7$ sulphonic acids (e.g. $MeC_6H_4SO_3H$, $MeSO_3H$, $CF_3SO_3H$), $C_1$-$C_7$ carboxylic acids (e.g. $C_6H_5COOH$, $CH_3COCOOH$, $CH_3COOH$, $C_2H_5COOH$) and the acidic resins such as the carboxylic or sulphonic acid supported on a methacrylic based or styrene based matrix (e.g. the one known under the tradenames Dowex® 50x8 or Amberlite® ICR 50).

According to a particular embodiment of the invention, said acid is a carboxylic derivative as described above.

As a base, to adjust the pH or to generate a buffer, typically an alkaline hydroxide such as NaOH or KOH, or an alkaline carbonate or bicarbonate such as $Na_2CO_3$ or $NaHCO_3$, may be used.

For the sake of clarity, by "aqueous reaction medium" it is meant here the medium wherein the reaction takes place. Therefore, the aqueous reaction medium comprises, or preferably consists of:
water and optionally a fully miscible solvent,
an appropriate amount of at least an acid or a base or of a mixture thereof, such as a buffer;
the compounds of formula (II) and (III), and optionally (I).

According to a particular embodiment of the invention, said aqueous reaction medium may comprise at least 10% of water, preferably at least 15% or even more between 20% and 60% of water, percentage being relative to its own weight. The above-mentioned fully miscible solvent may be present in amount ranging between 0% and 100%, percentage being relative to the weight of water. Typical examples of such solvents are tetrahydrofuran (THF), or a lower alcohol such as methanol, ethanol or a propanol.

According to a particular embodiment of the invention, both $R^1$ groups have the same meaning. According to a further embodiment both $R^1$ groups represent a methyl group and therefore the glyoxal (II) is methyl glyoxal, the acetol (III) is acetol (i.e. 1-hydroxy-2-propanone) and the dihydroxy-dione (I) is 3,4-dihydroxyhexane-2,5-dione.

The amount in which the acetol derivative (III) may be employed in the invention's process is typically comprised between 0.5 and 20 molar equivalents, relative to the glyoxal. According to a particular embodiment said amount may range from 2 to 10 molar equivalents, relative to the glyoxal.

The temperature at which the process of the invention can be carried out is comprised between 50° C. and 120° C., more preferably between 65° C. and 95° C. If necessary, the reaction can also be carried out in the presence of pressure, so as to react the higher temperature of the described ranges.

As mentioned above, the compound of formula (I) can be a valuable intermediate for the preparation of furanone derivatives and in particular, when $R^1$ and $R^2$ are both a methyl group, for the preparation of the flavor ingredient 4-hydroxy-2,5-dimethyl-3(2H)-furanone.

Therefore another object of the present invention is a process for the preparation of a furanone of formula

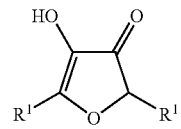

(IV)

comprising the following steps:
the preparation of a compound (I), as defined hereinabove, according to a process as described in the present invention; and
the cyclisation of said compound (I).

The cyclisation step can be performed according to any method known to a person skilled in the art. For example, one may cite a cyclisation method in the presence of a buffer such the ones described by Buchi et al. in *J. Org. Chem.*, 1973, 123, or by Selinov et al. in US2002/0111500, or by Briggs et al. in *J. Chem. Soc.* Perkin Trans. 1, 1985, 795.

EXAMPLES

The invention will now be described in further detail by way of the following examples, wherein the temperatures are indicated in degrees centigrade and the abbreviations have the usual meaning in the art.

Example 1

Experimental Procedure

A solution of methyl glyoxal 43% wt in water (2.00 g, 11.9 mmol), hydroxy-acetone (4.42 g, 59.7 mmol), and acetic acid (1.43 g, 23.8 mmol) in water (0.9 ml) were stirred during 16 hours at 70° C. (pH of the reaction medium was around 2.0). At the end of the reaction the reaction mixture was concentrated under reduced pressure giving 2.1 g of the crude 3,4-dihydroxyhexane-2,5-dione (56% purity measured by GC vs. internal standard). Crude 3,4-dihydroxyhexane-2,5-dione was distilled under reduced pressure to give 3,4-dihydroxyhexane-2,5-dione (1.56 g, 74% purity, 66% yield) as a pale yellow solid. The product obtained had the same $^1$H-NMR spectra as those described in Büchi et al, J. Org. Chem., 1973, 38, 123.

Following the same experimental procedure as above several, other experiments according to the invention were performed. The results are summarized in the Table 1.

TABLE 1

Aldol condensation between methyl glyoxal and Acetol to give 3,4-dihydroxyhexane-2,5-dione

| N° | Glyoxal (mmol.) | Acetol (m.e.)[1] | Solvent (ml) | Acid (m.e.)[1] | pH | T (°C.) | Time (h) | yield |
|---|---|---|---|---|---|---|---|---|
| 1 | 11.9 | 3 | none | Phosphate buffer | 5.5 | 70 | 6 | 32% |
| 2 | 11.9 | 3 | none | Phosphate buffer | 4.2 | 70 | 6 | 49% |
| 3 | 1.2 | 5 | none | $CH_3COCO_2H$ | 2.2 | 100 | 5 | 30% |
| 4 | 6.0 | 5 | none | $CH_3COCO_2H$ | 2.2 | 100 | 16 | 56% |
| 5 | 119 | 3 | $H_2O$ (30) | NaOH | 5.2 | 100 | 6 | 10% |
| 6 | 5.6 | 3 | $H_2O$ (1) | $H_3PO_4$ (0.05) | 0.8 | 100 | 6 | 28% |
| 7 | 5.6 | 3 | $H_2O$ (1) | HCl (0.05) | 0.8 | 100 | 6 | 42% |
| 8 | 5.6 | 3 | $H_2O$ (1) | $H_2SO_4$ (0.05) | 0.8 | 100 | 6 | 41% |
| 9 | 5.6 | 3 | $H_2O$ (1) | Dowex 50x8 | 2.1 | 100 | 6 | 45% |
| 10 | 66.6 | 3 | $H_2O$ (120) | AcOH (3) | 1.9 | 100 | 6 | 57% |
| 11 | 11.9 | 3 | $H_2O$ (2.5) | AcOH (3) | 1.9 | 70 | 16 | 64% |
| 12[2] | 50 | 2.5 | $H_2O$ (20) |  | 5.8 | 20 | 72 | 20% |
| 13[3] | 50 | 2.0 | $H_2O$ (30) |  | 3.5 | 40 | 90 | 12% | m.e. = molar equivalent;
[1] acid or buffer used to fix the pH of the reacting medium, amounts relative to methyl glyoxal
[2] comparative examples performed in the presence of $Zn(acac)_2$ at 0.08 m.e. (according to Example 1, Table 1, N°2 in WO 2006/048795)
[3] comparative examples performed in the presence of $Zn(acetate)_2$ at 0.10 m.e., acid used is AcOH, (according experimental conditions described in WO 2006/048795)

What is claimed is:

1. A process for the preparation of a compound of formula

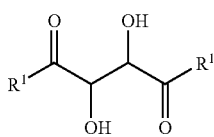

(I)

by aldol condensation, in an aqueous reaction medium, between a glyoxal of formula

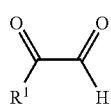

(II)

and an α-hydroxy ketone of formula

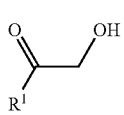

(III)

wherein each $R^1$ represents, simultaneously or independently from each other, a linear or branched $C_1$ to $C_5$ alkyl radical, with the aqueous reaction medium having a pH of between 0 and 6, and with the process carried out at a temperature of between 50° C. and the reflux temperature of the aqueous medium and in the absence of catalysts of formula $FeX_3$ or $MX_2$, wherein M is $Zn^{2+}$, $Mg^{2+}$, $Cu^{2+}$, $Fe^{2+}$ or $Ca^{2+}$ and X is a $C_1$-$C_7$ carboxylate, a halide or an acetylacetonate derivative of formula $[R^2COCHCOR^2]^-$, $R^2$ representing a $C_1$-$C_3$ alkyl group or a phenyl group.

2. The process of claim 1, which is free of any useful amount of catalysts of formula M(X)n, wherein n is 2 or 3, X is as defined in claim 1 and M is a transition or alkaline-earth metal.

3. The process of claim 1, wherein aqueous reaction medium has a pH of between 0 and 4.6.

4. The process of claim 1, which is carried out at a temperature of between 65° C. and 95° C.

5. The process of claim 1, wherein the pH of the aqueous reaction medium comprises an appropriate amount of at least an acid, a base or a mixture thereof, to regulate the pH.

6. The process of claim 5, wherein the acid is HCl, $H_2SO_4$, $H_3PO_4$, $C_1$-$C_7$ sulphonic acids (e.g. $MeC_6H_4SO_3H$, $MeSO_3H$, $CF_3SO_3H$), $C_1$-$C_7$ carboxylic acids or carboxylic or sulphonic acid resins.

7. The process of claim 5, wherein the base is an alkaline hydroxide or an alkaline carbonate or bicarbonate.

8. The process of claim 1, wherein each $R^1$ represents a methyl group.

9. A process for the preparation of a furanone of formula

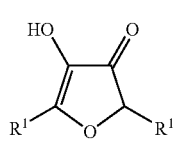
(IV)

which comprises:

preparing a compound of formula (I)

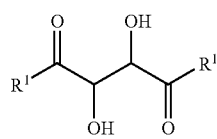
(I)

by aldol condensation, in an aqueous reaction medium, between a glyoxal of formula

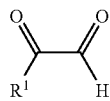
(II)

and an α-hydroxy ketone of formula

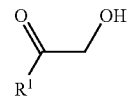
(III)

wherein each $R^1$ represents, simultaneously or independently from each other, a linear or branched $C_1$ to $C_5$ alkyl radical, with the aqueous reaction medium having a pH of between 0 and 6, and with the process carried out at a temperature of between 50° C. and the reflux temperature of the aqueous medium and in the absence of catalysts of formula $FeX_3$ or $MX_2$, wherein M is $Zn^{2+}$, $Mg^{2+}$, $Cu^{2+}$, $Fe^{2+}$ or $Ca^{2+}$ and X is a $C_1$-$C_7$ carboxylate, a halide or an acetylacetonate derivative of formula $[R^2COCHCOR^2]^-$, $R^2$ representing a $C_1$-$C_3$ alkyl group or a phenyl group; and cyclizing the compound (I).

* * * * *